(12) United States Patent
Shinar et al.

(10) Patent No.: US 7,718,130 B1
(45) Date of Patent: May 18, 2010

(54) INTEGRATED THIN-FILM SENSORS AND METHODS

(75) Inventors: Ruth Shinar, Ames, IA (US); Joseph Shinar, Ames, IA (US); Vikram L. Dalal, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 1072 days.

(21) Appl. No.: 11/401,274

(22) Filed: Apr. 11, 2006

Related U.S. Application Data

(60) Provisional application No. 60/670,248, filed on Apr. 12, 2005.

(51) Int. Cl.
*G01N 21/64* (2006.01)
*G01N 21/00* (2006.01)
*F21V 9/16* (2006.01)
*G01N 21/76* (2006.01)
*G02B 6/00* (2006.01)

(52) U.S. Cl. ............ 422/82.07; 422/82.05; 422/82.06; 422/82.08; 422/82.09; 422/82.11; 436/164; 436/172; 385/12; 250/458.1; 250/459.1

(58) Field of Classification Search ................ None
See application file for complete search history.

(56) References Cited

U.S. PATENT DOCUMENTS

| 6,331,438 B1 | 12/2001 | Aylott et al. |
| 2006/0132786 A1 | 6/2006 | Helbing |

*Primary Examiner*—Jill Warden
*Assistant Examiner*—Neil Turk
(74) *Attorney, Agent, or Firm*—Dickstein Shapiro LLP

(57) ABSTRACT

Integrated photoluminescence (PL)-based chemical and biological sensors are provided comprising a photodetector (PD), a long-pass filter, an excitation source, and a sensing element, all based on thin films or structures. In one embodiment the light source is an organic light emitting device (OLED) and the sensing element is based on thin films or solutions in microfluidic channels or wells. The PD and optical filters are based on thin film amorphous or nanocrystalline silicon and related materials. In another embodiment, sensor components are fabricated on transparent substrates, which are attached back-to-back to generate a compact, integrated structure.

24 Claims, 4 Drawing Sheets

INTEGRATED THIN-FILM SENSORS AND METHODS

This application claims the benefit of U.S. Provisional Application Ser. No. 60/670,248 filed on Apr. 12, 2005, the entire disclosure of which is incorporated herein by reference.

GOVERNMENT RIGHTS

The United States Government has certain rights in this invention pursuant to Contract Number ECS0428220 between the National Science Foundation and Iowa State University.

FIELD OF THE INVENTION

The present invention relates to luminescent chemical and biological sensors having structural integration of sensor components.

BACKGROUND OF THE INVENTION

Detection and quantification of analytes are of prime interest in medical, biochemical, analytical chemical, occupational safety, microelectronic, environmental, military, and forensic applications. Electrochemical sensors can be used for these applications. However, electrochemical sensors consume analytes, have long response times, are limited with regard to in vivo use, and are susceptible to poisoning by various contaminants. Optical sensing and probing are alternatives to electrochemical sensors. Various studies on optical methods of analyte detection have been reported in which a dye is immobilized in an analyte-permeable layer. In particular, these studies include sensors whose photoluminescence ("PL") is affected by the analyte. Such affects may include a change in the PL intensity, spectrum, decay time, or polarization.

Commercially available optical sensors typically employ inorganic single crystal III-V compound light-emitting diodes ("LEDs") as the light source. However, the need to incorporate optical components to convey light to the sensor and to collect the PL for readout increases complexity, size, and costs. Thus, single crystal III-V compound inorganic LEDs do not permit simple fabrication of integrated multisensor arrays.

In general, PL-based (bio)chemical sensors include a luminescent sensing element (the PL of which probes the analyte or agent), a light source that excites the PL of that element, a photodetector (PD), a power supply, and the electronics for signal processing. Light sources such as lasers or inorganic LEDs either may be difficult to integrate with the other components due to size, geometrical, or operational constraints, or they involve intricate integration procedures. In addition, they often generate heat, which can damage the sensing element or analyte.

Luminescent chemical and biological sensors detect changes in the PL intensity ($I_{PL}$) or lifetime ($\tau_{PL}$) of the sensing element caused by the analyte. In spite of potential widespread applications, the PD and light sources necessary to excite their PL typically have not been fully integrated with the sensing element. Consequently, the unintegrated devices are relatively bulky, costly, require trained operators, and are limited in their applications. As an example, the current commercial oxygen sensors for remote or local sensing, e.g., Ocean Optics FOXY sensor (see, e.g., www.oceanoptics.com), PreSense, and FCI Environmental Inc. employ GaN LEDs as the light source. The need to incorporate additional components such as optical fibers and their couplers to guide the light back and forth increases the size, cost, and complexity of the unit.

U.S. Pat. No. 6,331,438, the disclosure of which is incorporated by reference herein in its entirety, refers to an exemplary organic light-emitting device ("OLED") excitation source and sensing element for analyte detection. What is needed is further integration of the PD and filters to provide very compact, robust, inexpensive, and autonomous sensors for real world applications, including multianalyte monitoring.

BRIEF SUMMARY OF THE INVENTION

The invention provides structural integration of PL-based chemical and biological sensors, which results in very compact, field-deployable devices.

Exemplary structurally integrated components of the invention include a PD, a long-pass filter, an excitation source, and a sensing element. The PD and filter are preferably based, for example, on thin films of hydrogenated amorphous or nanocrystalline or microcrystalline silicon and its alloys.

In one embodiment, the PD, the filter, and the OLED are fabricated as alternating pixels on one side of a common transparent substrate and the solid matrix or solution-based sensing element is on the other side of the substrate.

In another embodiment, the PD, the filter, and the OLED are fabricated as alternating pixels on one side of a common substrate. The solid matrix or solution-based sensing element is formed on a separate substrate, which is attached back-to-back to the PD/filter/OLED substrate.

In other embodiments, the light source is an OLED and the sensing element is based on thin films or solutions in microfluidic channels or wells. The integration is achieved by fabricating the OLED on one side of a substrate and a solution-based sensing element on the other side of the substrate. In this embodiment, the PD and filter may be fabricated on a separate substrate that serves as a cover for microfluidic channels or wells.

In other embodiments, the invention provides a band-pass filter formed between the two separate substrates, which is capable of blocking an emitted light from the OLED from reaching the PD and allowing an emitted photoluminescence from the sensing element to reach the PD.

In other embodiments, the invention provides a PD that is a thin film of hydrogenated amorphous silicon germanium or nanocrystalline or microcrystalline silicon PIN device.

These and other features and advantages of the invention will become apparent from the following detailed description that is provided in connection with the accompanying drawings and illustrated exemplary embodiments of the invention.

DETAILED DESCRIPTION OF THE INVENTION

Figure 1:
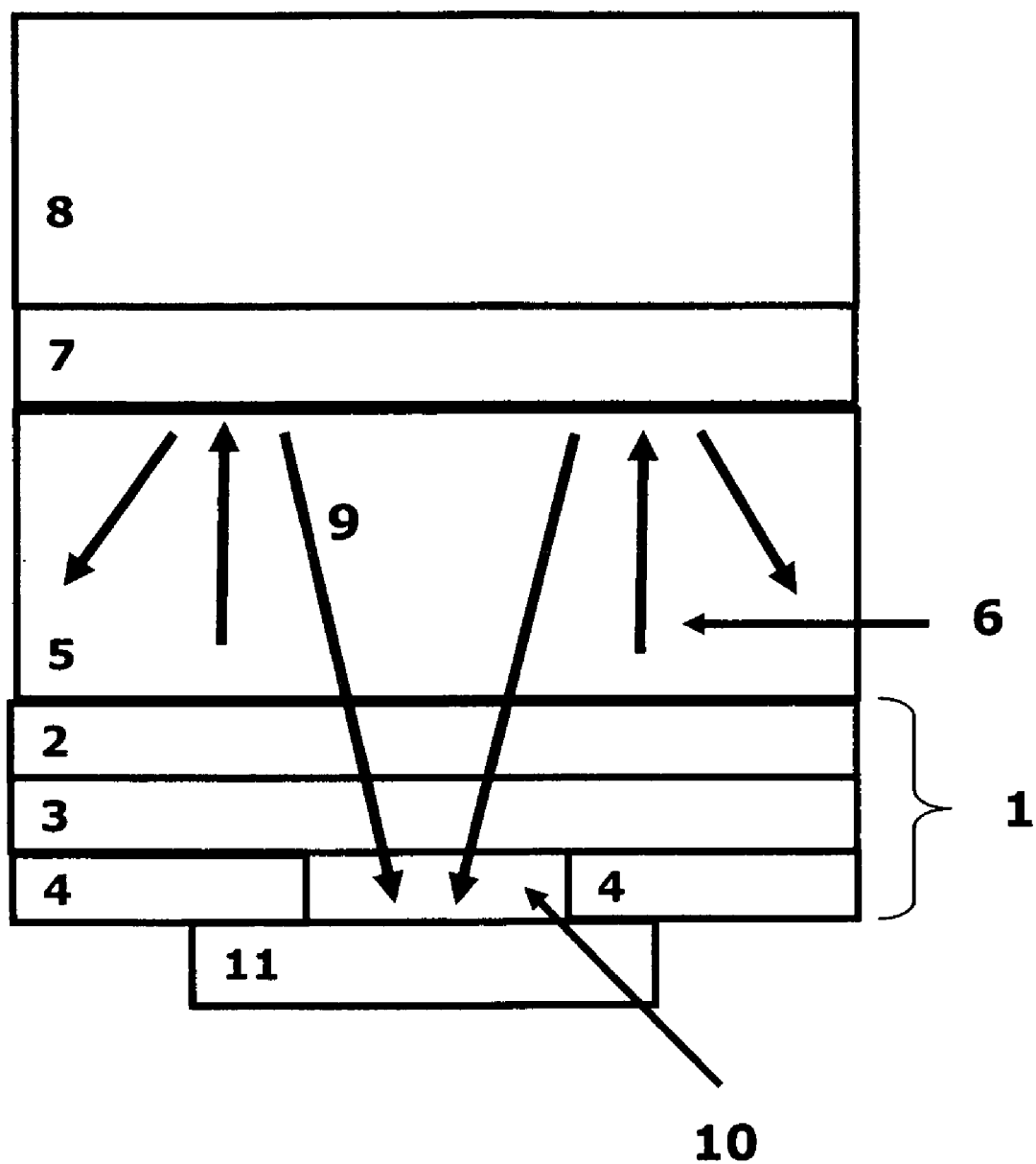
FIG. 1 illustrates an optical sensor according to the invention which has a back-detection geometry.

The optical probing and sensing devices of the present invention provide structural integration of sensor components preferably by fabricating all sensor components on, for example, a common substrate or substrates attached back-to-back. Components that can be integrated include, but are not limited to, the excitation source (e.g., an array of OLED pixels), the sensing element (e.g., a porous film with an embedded dye, surface immobilized species whose PL changes upon interaction with the agent, or microfluidic channels or wells with recognition elements in solution), the PD, and a long-pass filter (to prevent the OLED light from reaching the PD).

Such structurally integrated sensors are very compact, highly automated, portable devices, which address the next frontier in the development of high throughput, miniaturized sensors for multianalyte analysis in real world environments. In addition, this complete integration yields robust and inexpensive (eventually disposable) sensors for a variety of chemical and biological analytes. This integration also enhances other sensor attributes, such as detection sensitivity and response time, and using OLEDs reduces heat consumption and dissipation, which is often an issue for heat-sensitive sensing elements and analytes.

Embodiments of the present invention provide structural integration of the OLED, sensing element, PD, and filters. In one embodiment (the "back-detection" geometry), the OLED and PD pixels are fabricated on the same side of a common substrate. This embodiment is suitable for both solid state- and solution-based sensing elements. In this embodiment, the PD array, with associated long-pass hydrogenated amorphous silicon carbon (a-$Si_{1-x}C_x$:H) filters, can be fabricated and then the OLED pixels can be fabricated in the gaps between the PD pixels. The sensing element (solid state films or microfluidics for solutions) can be fabricated on a separate substrate and attached back-to-back to the OLED/PD substrate (see, e.g., FIG. 2).

In another embodiment (the "front-detection" geometry), the OLED array and the microfluidic channels or wells for a solution-based sensing element can be fabricated on different substrates attached back-to-back. The PD and its long-pass filter can be fabricated on a glass or plastic substrate that serves as a cover for the microfluidic channels or wells (see, e.g., FIG. 4). Access holes for liquid or gas can be generated in the cover. In an exemplary complete packaged device, the electronic circuitry, readout, and battery are "behind" the OLED or OLED/PD array. Hence, the whole device can be smaller than about 2"×3"×0.5," which is far more compact and potentially far less costly than any current commercial sensors.

In one preferred embodiment of the invention, the PD comprises a p-layer, an intrinsic layer, and a n-layer. In one example, the PD can be either a pin detector, or a nip detector, based on which side faces the incoming light first. If the p side faces incoming light, then it is referred to as a pin device. If the n side faces light, it can be referred to as a nip device. Each of the three exemplary layers (e.g., n-doped (n), p-doped (p), and intrinsic (i)) can be fabricated from a Group IV element or its alloy. In addition to the active semiconductor layers (p, i and n), the device can have appropriate ohmic contacts, with the layer facing incoming light being capable of transmitting in the wavelength region of the PL.

An exemplary OLED 1, as shown in FIG. 1, comprises a transparent conducting anode 2 made of indium tin oxide (ITO)-coated glass or plastic substrate 5. Other water-soluble transparent conducting substrate materials, such as doped polyaniline and poly-(3,4-ethylene dioxy-2,4-triphene)-polystyrene sulfonate (PEDOT-PSS), also yield high-performance anodes for an OLED 1. Further, an OLED 1 includes organic films 3, which comprise a hole transporting layer (HTL), an emitting layer, and an electron-transporting layer (ETL), and a low-work-function metal cathode 4. Under forward bias, electrons are injected from the low-work-function metal cathode 4 into the electron-transport layer (ETL). Similarly, holes are injected from the high-work-function ITO anode 2 into the hole-transport layer (HTL). Due to the applied bias, the electrons and holes drift towards each other, and can recombine in the emitting layer. Some of the recombination events result in radiative excited states. The radiative decay provides the electroluminescence 6 (EL) of the device. An OLED 1 is easily fabricated in low vacuum utilizing fabrication techniques such as thermal evaporation and spin coating. The thickness of the whole OLED 1 may be, for example, less than 0.5 microns. In addition, the OLED 1 may be operated in a pulsed mode, which will increase its lifetime and generate much less ohmic heat, thus rendering it particularly suitable for heat-sensitive sensing elements and analytes.

The OLED/(sensing element)/PD integration approaches of the present invention result in new sensor platforms for PL-based detection of chemical and biological agents. The preferred platforms are designed for extremely compact and inexpensive sensor microarrays for high throughput, multianalyte detection, in vitro and in vivo.

"Back-Detection" Geometry Devices

The devices according to the invention may be constructed using various light transmission geometries. FIG. 1 depicts an OLED-based integrated optical sensor according to the invention which has a back-detection geometry. Specifically, the schematic shows an OLED 1 emitting EL 6 through a substrate 5 to a photoluminescent sensor layer 7. The sensor layer 7 is exposed to a gas or liquid cell medium 8, which may or may not contain an analyte. If an analyte is present, the sensor layer 7 emits a different PL 9 than if no analyte is present. PL 9 travels through the substrate 5, the ITO anode 2, the organic films 3, and through the opening 10 of the metal cathode 4, to be collected by a photodetector 11.

Figure 2:
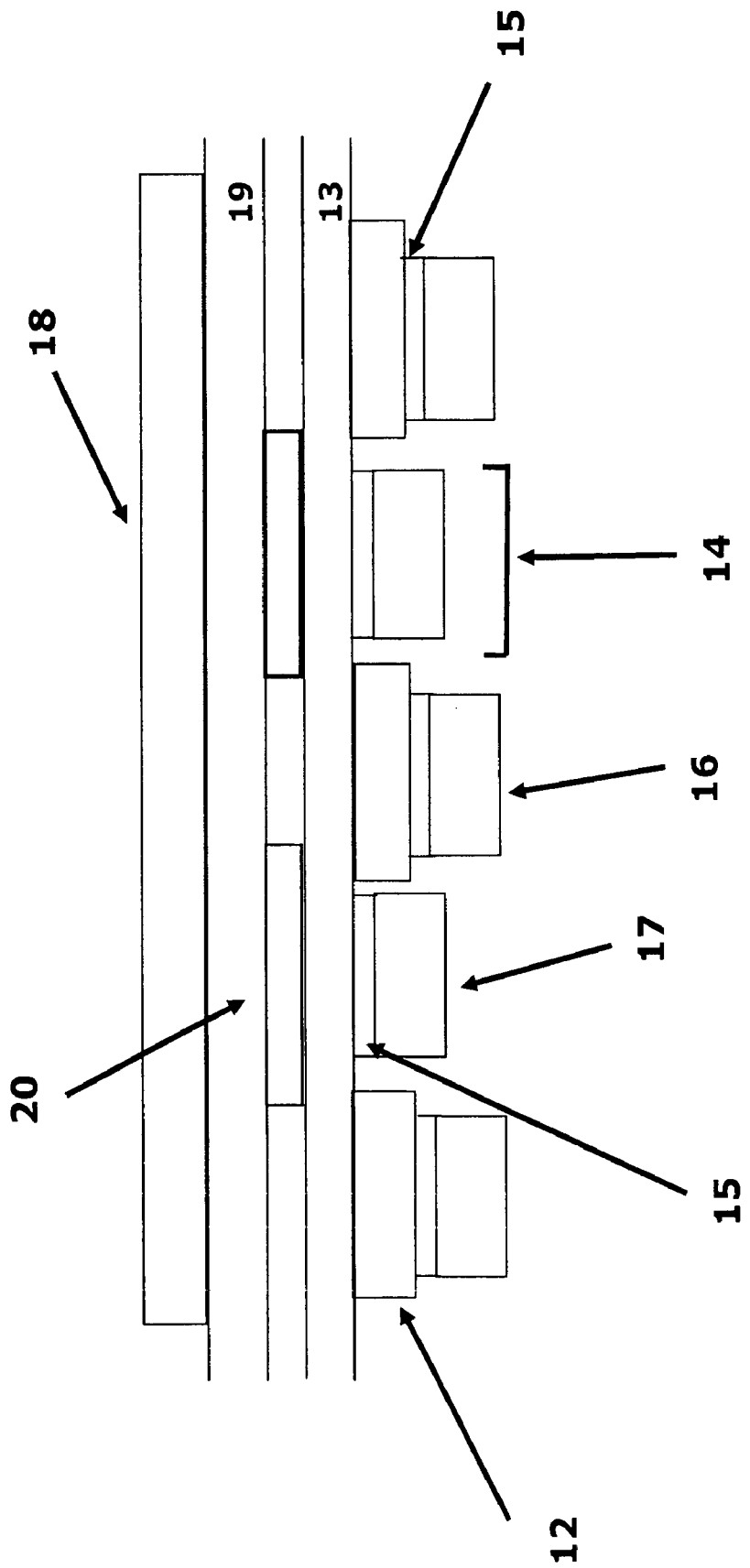
FIG. 2 illustrates an exemplary fully integrated back-detection geometry device.

An exemplary fully integrated back-detection-geometry structure is shown in FIG. 2. In this embodiment, the OLED 17 and PD 16 are fabricated on the same side of a common first substrate 13. The sensing element 18, which is a solid state film or microfluidic for solutions, can be fabricated on a second substrate 19 and attached back-to-back to the first substrate 13, separated by a band-pass filter 20 between the first substrate 13 and the second substrate 19. Another embodiment (not shown) provides a sensing element 18 on the opposite side of the first substrate 13.

A preferred back-detection device is formed by depositing a hydrogenated amorphous silicon carbon layer 12 (or long-pass filter 12) with an optical gap of about 2.3 eV on a first substrate 13 by plasma-enhanced chemical vapor deposition (PECVD) or by electron cyclotron resonance (ECR). The hydrogenated amorphous silicon carbon layer 12 can be deposited through a mask to yield a pattern of about 6 millimeter-wide strips separated by about 6 millimeter-wide openings 14, or uniformly over the glass or plastic substrate 13, and then etched to form such strips using photolithography. Embodiments of the present invention utilize the distinct bandgaps of hydrogenated amorphous silicon carbon (a-$Si_{1-x}C_x$:H), as well as other materials, such as a-$Si_{1-x}Ge_x$:H, and μc-Si:H. In one example, the optical bandgap of hydrogenated amorphous silicon carbon layer 12 increases from about 1.7 eV to about 2.5 eV as the carbon and hydrogen content increase from about 3 to about 20 atomic percent. Hence, a 1 μm hydrogenated amorphous silicon carbon layer 12 is used as a long-pass filter with very high rejection ratios, to block the blue and green OLED emission (at λ<520 nm) from the PD 16 but pass the red PL from the sensing element 18 (at λ>600 nm) and generate a photocurrent in the PD 16.

Further, as shown in FIG. 2, strips of an ITO layer 15 are deposited on portions of the long-pass filter 12 and on portions of the first substrate 13 within openings 14. About 3 millimeter-wide ITO strips 15 of about 200 nanometers thick are deposited by RF sputtering of an ITO target through a mask, to provide the anodes for both the PD 16 and OLED 17. In one embodiment, the PD 16 is a thin film of hydrogenated amorphous silicon germanium (a-Si$_{1-x}$Ge$_x$:H, x≦0.3) or nanocrystalline or microcrystalline silicon (μc-Si:H) PIN device. The PIN layers of the PD 16 are deposited on the ITO strips 15 on the portions of the long-pass filter 12. In another embodiment, the long-pass filter 12 can be fabricated opposite the PD 16, on the other side of the first substrate 13. The PD 16 is about 3 millimeters wide and has a thickness in a range of about 0.5 micrometers to about 2 micrometers. This exemplary PIN PD 16 exhibits high sensitivity for emitted light of commonly used fluorophores. In addition, the dark current of a-Si:H is typically very low (~$10^{-11}$ A/cm$^2$ at 25° C.), resulting in low noise. Additionally, the p-layer of the PIN structured PD 16 can serve as a filter that absorbs the OLED blue and/or green emission by fabricating a thick p-layer with a bandgap larger than that of the intrinsic layer of the PIN structure, but smaller than that of green OLED light. The p-layer can also have a graded bandgap. The PIN PD 16 can be fabricated by e.g., PECVD and sputtering techniques in a reactive hydrogen atmosphere with various dopants in the p- (B, Al, Ga) and n- (P, Sb, As) layers and various transparent contact layers (e.g., ITO, tin oxide, zinc oxide).

The organic layers (not shown) of the OLED 17 are deposited on the other ITO strips 15 on the portions of the first substrate 13. The layers of the OLED 17 are about 5 millimeters wide and the deposition of the layers are preferably followed by about a 10 Angstrom-thick CsF buffer layer and the electron-injecting aluminum metal layer (not shown). About 3 millimeter wide aluminum strips (not shown), separated by about 3 millimeter wide gaps, are then deposited through a mask perpendicular to the ITO strips 15. This yields an alternating pattern of PD 16 and OLED 17 on the same side of a common substrate 13.

In another embodiment, the exemplary procedure described above can be used to fabricate matrix arrays of OLED pixels using appropriate masks. This structure enables simple encapsulation of the OLED array (by bonding it to a glass cover with epoxy) and enables an appropriate bias that is applied simultaneously to any set of OLED pixels.

The features of the embodiments of the invention are particularly advantageous. For example, due to the waveguiding effect of the OLED's structure 17, internally reflected light from the OLED 17 will be emitted sideways, through the edges of an OLED 17.

The procedure described above completes the "bottom" side of the structure shown in FIG. 2. In the next step, a sensing element 18 is fabricated on the other side of the first substrate 13, or on a separate second substrate 19 attached back-to-back to the first substrate 13. A band-pass filter 20 can be sandwiched between the first substrate 13 and the second substrate 19. A blue (e.g., tris(4,7-diphenyl-1,10-phenanthroline for Ru(II), Ru(dpp), which is excited by a blue OLED 17) or green (for e.g., Pt octaethyl porphyrin, PtOEP, which is excited by a green OLED 17) band-pass filter 20 will block the long-wavelength tail (at λ>520 or 560 nm, respectively) of the OLED emission, so the red light reaching the PD 16 will be due to the sensing element 18 PL only.

To maximize the EL that reaches the sensing element 18 and minimize the reflectance of the EL and PL from the surface of the substrates 13 and 19, these surfaces can be coated with an anti-reflecting coating, prior to the fabrication of the PD 16/OLED 17 structure. The "top surface" of the sensing element 18 can also be coated with a reflecting film, to maximize the PL that will reach the PD 16.

In another embodiment in accordance with the invention, ring-shaped long-pass filters 12 and a-Si$_{1-x}$Ge$_x$:H or μc-Si:H PDs 16 can also be fabricated. The OLEDs 17 are then fabricated inside these rings.

"Front-Detection" Geometry Devices

Figure 3:
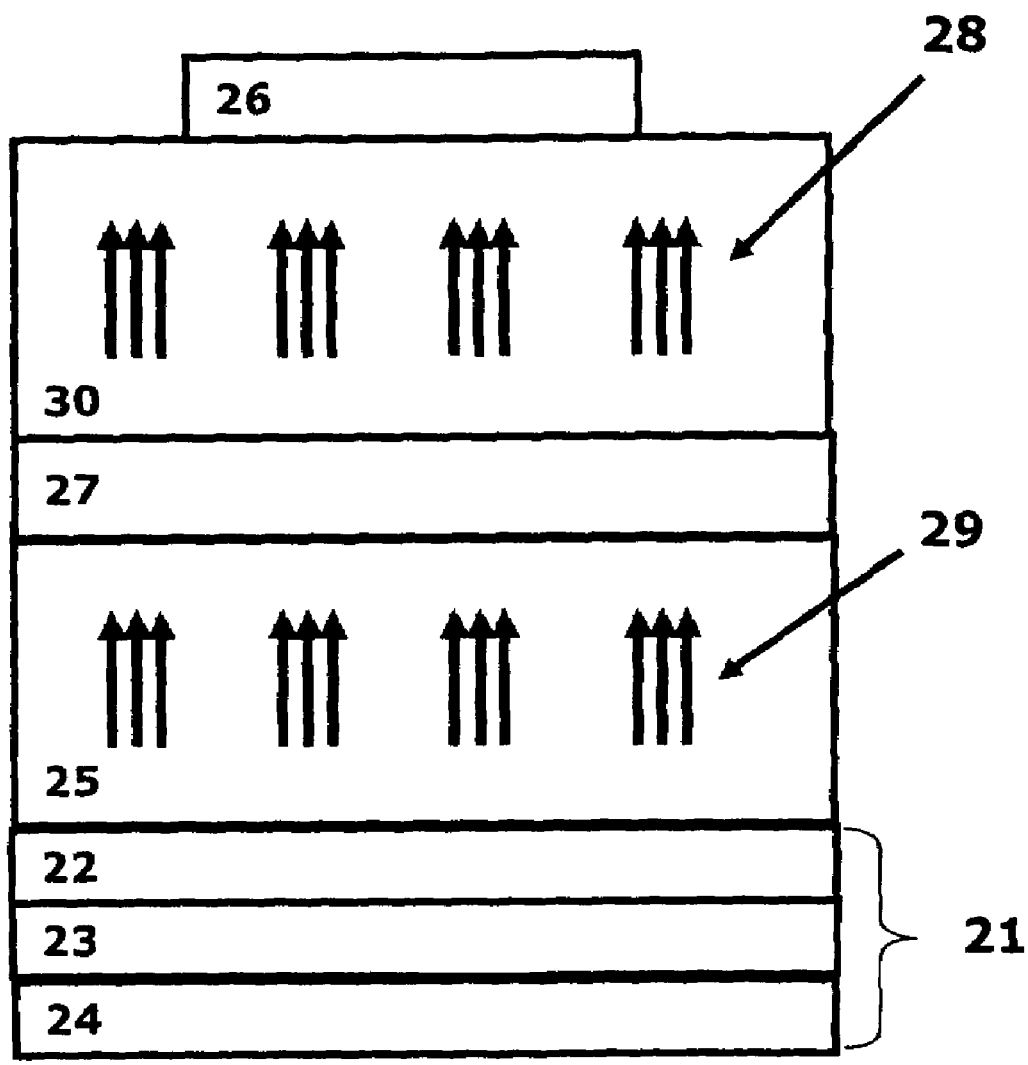
FIG. 3 illustrates an optical sensor according to the invention which has a front-detection geometry.

Another type of light transmission geometry, the front-detection or direct transmission geometry, is shown schematically in FIG. 3. FIG. 3 depicts specifically an OLED 21 and a PD 26 located on opposite sides of a photoluminescent sensor layer 27. The OLED 21, comprising the ITO anode 22, organic films 23, and metal cathode 24, emits a light 29 across a substrate 25 into sensor layer 27. The sensor layer 27 is exposed to a gas or liquid cell medium 30, which may or may not contain an analyte. If an analyte is present, the analyte interacts with the sensor layer 27 to alter its optical characteristics. The optical response 28, as a result of emitted light 29 and the presence of an analyte, is detected by photodetector 26.

Figure 4:
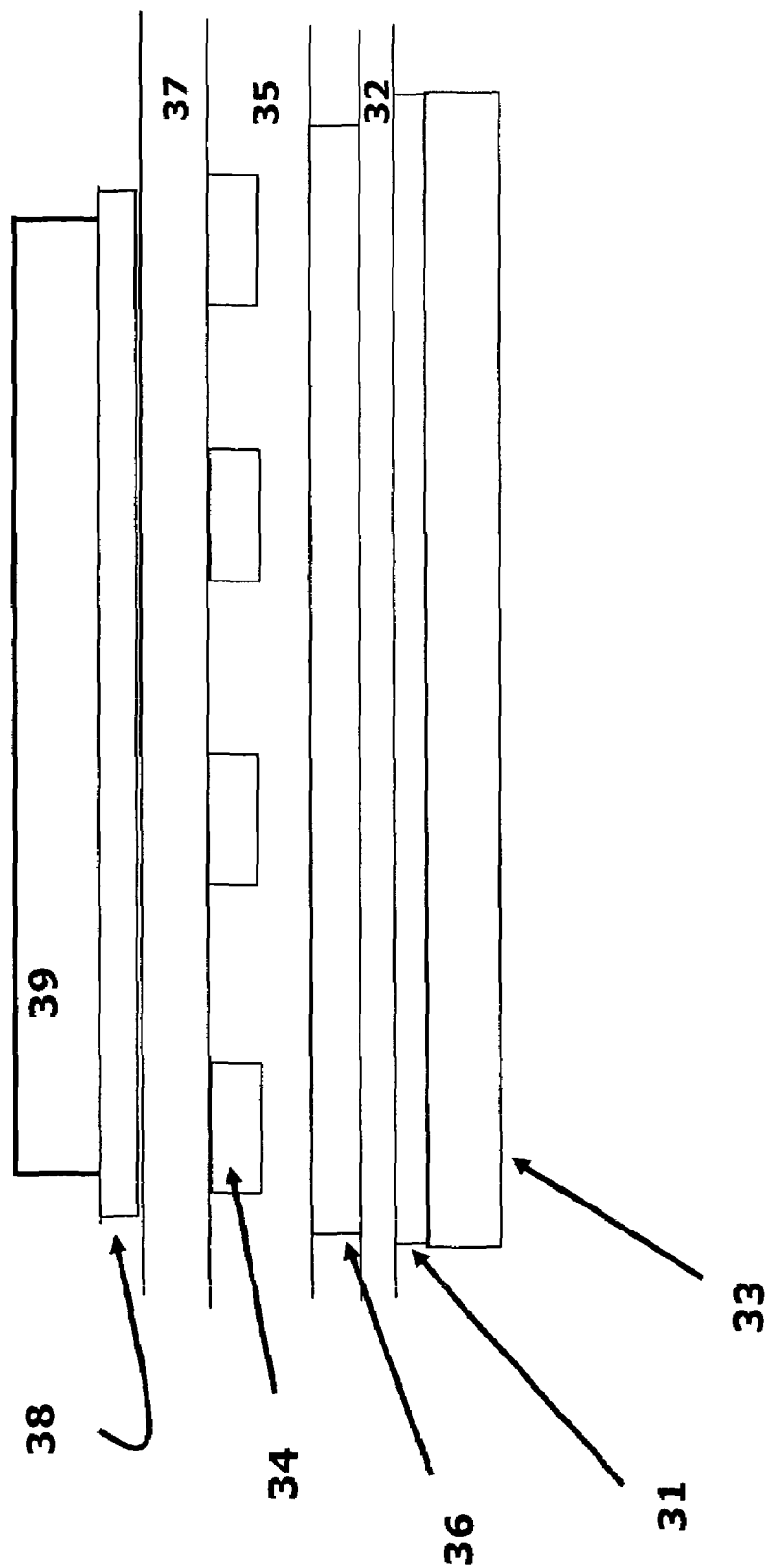
FIG. 4 illustrates an exemplary fully integrated front-detection geometry device.

FIG. 4 illustrates the structure for one embodiment of the front-detection geometry configuration. Preferably, front-detection geometry is used for solution-based sensing elements. Fabrication preferably begins, for example, with an ITO layer 31 covering a first substrate 32 to generate an OLED pixel array 33, as described above. Microfluidic channels or wells 34 can be generated, with openings (for dispensing liquid) from the side, for example, using standard procedures on a separate second substrate 35, which is made of glass or plastic (e.g., poly(dimethylsiloxane) (PDMS)). These channels or wells 34 contain the sensing element (not shown). The OLED array 33 and sensing element can be attached back-to-back with a suitable band-pass filter 36 sandwiched between the first substrate 32 and the second substrate 35, to block the long wavelength tail of the OLED emission from the PD 39. A third substrate 37 can then be used to fabricate on one side a PD 39 and a long-pass filter 38 made of hydrogenated amorphous silicon carbon. The other side of the third substrate 37 contacts the sensing element (not shown), serving as a cover for the microfluidic channels or wells 34. Access holes, for introducing the analyte can be fabricated in the lid, which can be bonded to the sensing element by an oxygen plasma.

The following examples further describe and demonstrate features of the present invention. The examples are given solely for illustration and are not to be construed as a limitation of the present invention.

Example

Manufacture of a Preferred Structurally Integrated Sensor

This exemplary OLED detector comprises a PIN-type device, with a semi-transparent contact deposited on the p-layer. The first layer deposited may be the semitransparent contact, for example ITO. The layer is deposited using, for example, sputtering in Ar atmosphere from appropriate ITO targets. This layer is followed by the deposition of a buffer layer, for example, zinc oxide (ZnO), whose function is to prevent interaction between the ITO layer and the following p-layer. The thin ZnO layer, which may be doped, for example with aluminum, is deposited using sputtering. The p-layer is deposited on the ZnO layer using PECVD techniques, using either RF glow discharge techniques, or ECR deposition techniques. The gases used for depositing the p-layer, which is made from an amorphous silicon-carbon alloy, are silane, hydrogen, methane, helium, and diborane, with diborane serving as the dopant. The ratio of methane to silane is adjusted to achieve a desired bandgap of the amorphous silicon. For example, if the OLED emission wavelength is 550 nm, and the fluorescent wavelength is 700 nm, the p-layer would be of such a wavelength as to absorb most (98+%) of the emission of 550 nm radiation. The thickness and bandgap of the p-layer are adjusted so as to achieve this high absorption of 550 nm wavelength. In this example, the p-layer would be transparent to the 700 nm wavelength.

Thin layers of isolated, confined, e.g., Al strips can be fabricated near the OLED, to block the OLED edge emission (or OLED radiation) from reaching the PD.

The p-layer can be followed by deposition of an exemplary intrinsic layer whose function is to absorb efficiently most of the radiation emitted by the fluorescent medium. The intrinsic layer can absorb, for example, the 700 nm radiation and can be made from an amorphous alloy of silicon and germanium with hydrogen, denoted by a-(Si,Ge):H. The bandgap of this alloy, in this example, is adjusted to be 1.5 eV. This alloy can also be deposited using for example, the RF glow discharge from a mixture of silane, germane, and hydrogen. Alternatively, gases such as disilane, germanium fluoride, or any other suitable gas can be used to produce a-(Si,Ge):H. The deposition temperature can be around 250° C. The pressure in the reactor can be maintained at about 50 mTorr. The thickness of the layer is about 0.5 micrometers. This intrinsic layer may be graded in bandgap if desired to increase carrier collection.

The intrinsic i-layer can be followed by deposition of a n-doped layer, made with, for example the same a-(Si,Ge):H alloy composition, using, for example, the same deposition techniques described herein. The n-type doping can be achieved using a dopant gas phosphine. Alternatively, to allow for back-reflection of photons into the intrinsic layer, the n-layer can be made from an a-(Si,Ge):H alloy with a larger bandgap than the bandgap of the intrinsic layer. This larger bandgap can be achieved by reducing the germane/silane ratio during deposition compared to the ratio used during the deposition of the intrinsic layer.

The n-layer can be followed by depositing a reflecting back contact layer, such as aluminum or silver, or a combination of conducting layers such as ITO/Al which enhance reflection of photons back into the device.

It is recognized that the above description is simply an example of how the device may be made. Alternative deposition schemes, such as sputtering or chemical vapor deposition of disilane and germane, can be used to make the various active layers in the device (p-, i-, and n-layers).

A further embodiment of the device may include multiple p-layers, arranged so that the first (p1) layer may be of a slightly larger bandgap so as to be able to absorb most of the incoming OLED radiation, whether coming sideways or from the top, and the second (p2) layer is of a slightly smaller bandgap to better match the bandgap and the valence band edges with the intrinsic layer. By having such a two p-layer arrangement, potential current collection problems related to a discontinuity in valence band between the single p-layer with a larger gap and the intrinsic layer may be minimized.

In addition to the amorphous alloys described above, it is possible to also use nanocrystalline (nc) materials such as nc-Si:H, nc-(Si,Ge):H, nc-(Si,C):H, and nc-(Ge,C):H as the p-, and n-layers in the device. It is also possible to use hybrid devices, where, for example, the p-layer may be amorphous, the i-layer is nanocrystalline, and the n-layer is amorphous. The example above also can provide a p-layer made from a-Si:H, an i-layer made from nc-(Si,Ge):H, and an n-layer made from a-Si:H.

The above description and drawings illustrate preferred embodiments that achieve the objects, features and advantages of the present invention. It is not intended that the present invention be limited to the illustrated embodiments. Any modification of the present invention that comes within the spirit and scope of the following claims should be considered part of the present invention.

What is claimed as new and desired to be protected by Letters Patent of the United States is:

1. An optical sensor for detection of an analyte of interest, said optical sensor comprising:
    a first substrate;
    a hydrogenated amorphous silicon carbon layer having a plurality of gaps on said first substrate;
    a plurality of strips of transparent electrode on a portion of said hydrogenated amorphous silicon carbon layer and on a portion of said first substrate within said gaps;
    a photodetector for detecting photoluminescence, and arranged on at least one of said transparent electrode strips on said portion of said hydrogenated amorphous silicon carbon layer; and
    an excitation source for emitting electroluminescence, and arranged on at least another of said transparent electrode strips on said portion of said first substrate within said gaps; and
    a sensing element arranged to emit said photoluminescence to said photodetector and arranged to receive said electroluminescence from said excitation source.

2. The optical sensor according to claim 1, wherein said first substrate comprises glass or plastic.

3. The optical sensor according to claim 1, wherein said hydrogenated amorphous silicon carbon layer has a thickness in the range of about 0.1 micrometers to about 1 micrometer.

4. The optical sensor according to claim 1, wherein said hydrogenated amorphous silicon carbon layer is capable of blocking emitted electroluminescence from said excitation source from reaching said photodetector.

5. The optical sensor according to claim 1, further comprising a plurality of aluminum strips fabricated near said excitation source to block edge emission from said excitation source from reaching said photodetector.

6. The optical sensor according to claim 1, wherein said photodetector comprises PIN layers.

7. The optical sensor according to claim 6, wherein said photodetector comprises microcrystalline silicon.

8. The optical sensor according to claim 6, wherein said photodetector comprises nanocrystalline silicon.

9. The optical sensor according to claim 6, wherein said photodetector comprises hydrogenated amorphous silicon germanium.

10. The optical sensor according to claim 6, wherein said photodetector has a thickness in the range of about 0.5 micrometers to about 2 micrometers.

11. The optical sensor according to claim 1, wherein said excitation source comprises an array of organic light emitting device pixels.

12. The optical sensor according to claim 11, wherein said excitation source has a thickness of less than about 0.5 microns.

13. The optical sensor according to claim 11, wherein said excitation source emits electroluminescence in a pulsed mode.

14. The optical sensor according to claim 1, wherein said strips of transparent electrode on said portion of said hydrogenated amorphous silicon carbon layer and on said portion of said first substrate within said gaps is configured to provide an anode for said excitation source and for said photodetector.

15. The optical sensor according to claim 14, wherein said excitation source comprises said anode, a hole transporting layer, an emitting layer, an electron-transporting layer, and a cathode.

16. The optical sensor according to claim 1, wherein said photodetector and said excitation source are on a same side of said first substrate.

17. The optical sensor according to claim 16, wherein said photodetector and said excitation source are fabricated in an alternating pattern.

18. The optical sensor according to claim 16, wherein said sensing element is fabricated on one side of said first substrate and said photodetector and said excitation source are on an opposing side of said first substrate.

19. The optical sensor according to claim 16, further comprising:
    a band-pass filter, wherein said band-pass filter is fabricated on one side of said first substrate and said photodetector and said excitation source are on an opposing side of said first substrate;
    a second substrate on said band-pass filter; and
    a sensing element on a surface of said second substrate.

20. The optical sensor according to claim 19, wherein said sensing element absorbs electroluminescence emitted from said excitation source.

21. The optical sensor according to claim 19, wherein said sensing element when exposed to a medium is configured to emit a photoluminescence response to said photodetector indicating an absence or presence of an analyte.

22. The optical sensor according to claim 19, wherein said band-pass filter is capable of blocking an emitted electroluminescence from said excitation source from reaching said photodetector and allowing an emitted photoluminescence from said sensing element to reach said photodetector.

23. The optical sensor according to claim 1, wherein said transparent electrode comprises indium tin oxide.

24. The optical sensor according to claim 18, wherein said sensing element comprises a plurality of microfluidic channels.

* * * * *